United States Patent [19]

Stoy et al.

[11] Patent Number: 5,285,962
[45] Date of Patent: Feb. 15, 1994

[54] METHOD AND APPARATUS FOR AUTOMATICALLY TRANSFERRING AND MEASURING WET STEAM BETWEEN MULTIPLE CONSTANT DEMAND USERS

[75] Inventors: James R. Stoy, Missouri City; James L. G. Schrodt, Houston, both of Tex.; Stephen S. Wheeler, Bakersfield, Calif.

[73] Assignee: Texaco Inc., White Plains, N.Y.

[21] Appl. No.: 966,819

[22] Filed: Oct. 26, 1992

[51] Int. Cl.⁵ .............................................. F24D 1/00
[52] U.S. Cl. ...................................... 237/9 R; 237/67
[58] Field of Search .................. 237/9 R, 67, 68, 2 R, 237/6; 236/9 A, 1 B

[56] References Cited

U.S. PATENT DOCUMENTS 4,836,032 6/1989 Redus et al. ..................... 73/861.04

FOREIGN PATENT DOCUMENTS 2429388 2/1980 France ................................. 237/13

Primary Examiner—Henry A. Bennet
Attorney, Agent, or Firm—James L. Bailey; Russell J. Egan

[57] ABSTRACT

A system for automatically controlling the quantity and quality of steam to a plurality of constant demand customers has a steam generating source, and pressure regulator means and steam mass flow measurement means between each constant demand customer and the steam generating source.

2 Claims, 1 Drawing Sheet

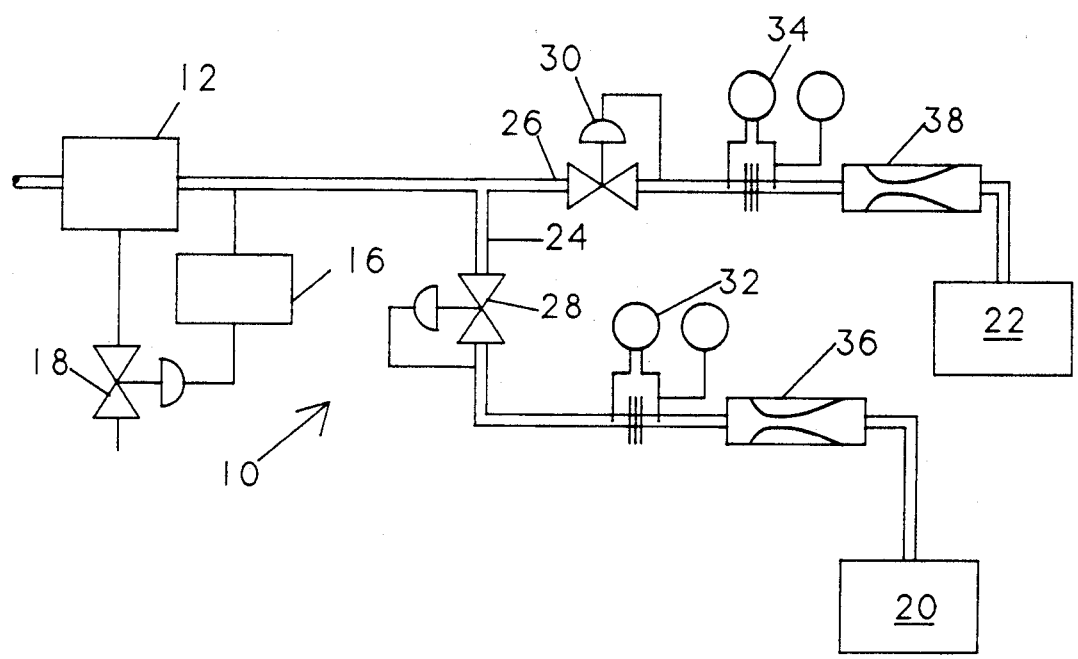

METHOD AND APPARATUS FOR
AUTOMATICALLY TRANSFERRING AND
MEASURING WET STEAM BETWEEN MULTIPLE
CONSTANT DEMAND USERS

BACKGROUND OF THE INVENTION

1. The Field of the Invention

The present invention pertains to a system allowing wet steam to be allocated between multiple constant demand users and, in particular, to system which will measure the mass rate and quality of wet steam delivered to each user to facilitate proper charging for steam usage.

2. The Prior Art

There are many instances when wet steam supplied from a single generating source is divided among multiple users of the steam for whatever their purpose. Thus it is important to be able to divide steam between multiple users and to allocate the steam to each user according to a scheme which is defined by the arrangement of a custody transfer system within an overall steam distribution piping system.

It can be appreciated that wet steam will normally leave the steam generator or source at a known quality, pressure and mass flow rate. It is important, therefore, as a matter of economic practicality that a means be instituted to control distribution of the steam. It is desirable that this be automatic to allocate steam between a multiplicity of user according to predetermined allocation schemes, such as distribution to multiple constant demand users. The purpose of such a custody transfer system would be to monitor each user's consumption of steam such that the user will be charged only for the amount of steam it actually consumes.

The measurement or monitoring of steam quality is important to determine steam usage for proper billing. Steam quality is a direct measurement of the heat contained in the steam and therefore represents the amount of fuel used to generate the steam and thus its cost.

In brief, it is desirable that the quality of steam, that is the mass of the steam vapor divided by the total mass, and that the mass flow rate be known and that the amount of steam consumed by each user likewise be known.

SUMMARY OF THE INVENTION

The present invention concerns a method by which a supplier of wet steam (less than 100% quality) may allocate and measure the mass rate and quality (vapor mass fraction) of steam delivered to multiple constant demand steam users. The method involves the combined use of at least two steam flow measurement systems; at least two pressure regulating valves; and means to collect record, and process data from the individual measuring systems. This invention has the capability of allocating steam according to a preset scheme according to the type and number of users.

BRIEF DESCRIPTION OF THE DRAWINGS

The present invention will now be described, by way of example, with reference to the accompanying drawing in which:

FIG. 1 is a schematic diagram of a multiple constant demand customer configuration of the present invention.

DETAILED DESCRIPTION OF THE PRESENT INVENTION

The subject system is specifically designed to handle wet steam and operates automatically in allocating steam to the various steam customers and measure each allocation. The present system is installed such that each one of multiple steam customer receives a constant mass rate of steam at the available steam quality.

U.S. Pat. No. 4,836,032, the disclosure of which is incorporated herein by reference, describes a system to simultaneously measure mass rate and steam quality of two phase steam by utilizing a critical flow device such as a venturi in conjunction with a common orifice type flowmeter. The steam mass rate passing through the venturi is described by the equation:

$$M = \frac{K_v P c^2}{X^a}$$

Where:
M = Steam Mass Rate
$K_v$ = Empirically Derived Flow Coefficient
P = Steam Pressure Upstream of Venturi
c = Venturi Throat Diameter
X = Steam Quality
a = Empirically Derived Exponent It should be noted that in order for the above equation to hold true, the venturi must be operating in critical flow. Critical flow, for purposes of this discussion, is defined as the flow rate necessary to achieve a pressure drop across the venturi equal to or less than the critical pressure ratio. The critical pressure ratio is the maximum ratio of downstream to upstream pressure at which mass rate is independent of downstream pressure. U.S. Pat. No. 5,141,055 describes a venturi design which enables the critical pressure ratio to be as high as 0.85. The disclosure of this patent is incorporated herein by reference. Several devices are capable of operating in critical flow and thus can be substituted for the venturi described above. The venturi is used solely by example and the scope of the invention is not limited thereto.

The steam mass rate flowing through the orifice meter is described by the equation:

$$M = \frac{K_o d^2}{\sqrt{1-B^4}} * \sqrt{\frac{dP}{X^b V_{fg} - V_f}}$$

Where:
M = Steam Mass Rate
$K_o$ = Empirically Derived Flow Coefficient
d = Orifice Diameter
B = Orifice Meter Beta Ratio (d/D)
D = Orifice Meter Run Inside Diameter
X = Steam Quality
b = Empirically Derived Exponent
dP = Orifice Meter Differential Pressure
$V_{fg}$ = Steam Specific Volume of Evaporation
$V_f$ = Steam Specific Volume of the Liquid Phase The two above equations are both solvable for steam mass rate in terms of steam quality. Since, in general, neither mass rate nor quality is known, the two equations may be solved simultaneously for mass rate and quality. One method which has been successfully demonstrated is the Newton-Raphson iterative solution.

Note that the venturi equation implies that the mass rate through the venturi is directly proportional to the pressure upstream of the venturi. It is this aspect of the venturi's behavior that is exploited by this invention.

The present invention 10, shown in FIG. 1, has a steam source 12 connected to a source of feed water (not shown) and a pressure controller 16 and regulator valve 18 connected between the fuel supply (not shown) and the output of the steam source 12. Each of the constant demand customers 20, 22 is connected by a feed line 24, 26 each containing a pressure regulator 28, 30, a two phase orifice meter 32, 34 and a critical flow venturi 36, 38.

FIG. 1 depicts the system configured to supply steam at a constant mass rate and quality simultaneously to several customers. This configuration allows each customer to adjust the steam mass rate, at available quality, to a constant value and the system automatically compensates for demand changes by other users. Thus each customer on the system is effectively isolated from all other customers. The mass rate and quality of steam delivered to each customer is measured by the orifice-venturi meter run at the inlet to each customer's piping system. This configuration requires that the steam source vary its output to match the sum of the individual customer demands. This can be accomplished with conventional boiler control strategy which is not a part of this invention.

The present invention may be subject to many modifications and changes, which will be apparent to one skilled in the art, without departing from the spirit or essential characteristics thereof. For example, the above discussed embodiment refers to two customers only for convenience in illustration. Any number of customers, up to the capacity of the system, may be connected and served by the system. The present embodiment is therefore to be considered in all respects as illustrative and not restrictive of the scope of the invention as defined by the appended claims.

We claim:

1. A method for automatically controlling the quantity and quality of steam delivered to a plurality of constant demand customers from a single steam source, said method comprising the steps of:
   providing a wet steam generating means;
   providing means to measurement the quality and quantity of steam generated by said generating means;
   providing a plurality of constant demand customers;
   providing pressure regulator means between each said constant demand customer and said steam generating means;
   providing steam flow measurement means for each of said constant demand customers;
   generating wet steam at said generating means; and
   feeding said wet steam to said constant demand customers with each said constant demand customer adjusting a respective pressure regulator whereby the system automatically compensates for demand changes by the other constant demand customers.

2. A system for automatically controlling the quantity of wet steam delivered to a plurality of constant demand customers from a single wet steam source, said system comprising:
   a plurality of constant demand customers;
   wet steam generating means operatively connected to a feed water source;
   means to measure the quality and quantity of steam generated by said steam generating means;
   a like plurality of steam flow measurement systems each connected between an output of said steam source and a respective constant demand customer to determine the quality of steam generated by said source; and
   a like plurality of pressure regulator means each connected between a respective constant demand customer and said steam source whereby each of said constant demand customers determines its own steam needs and the system compensates for demand changes by other constant demand customers.

* * * * *